United States Patent [19]

Febvre

[11] 4,017,361
[45] Apr. 12, 1977

[54] PROCESS FOR OBTAINING CONTINUOUS LINES OF TUMORAL CELLS IN VITRO

[75] Inventor: Henri Lucien Febvre, Paris, France

[73] Assignee: Choay S.A., Paris, France

[22] Filed: Mar. 20, 1975

[21] Appl. No.: 560,241

[30] Foreign Application Priority Data

Mar. 27, 1974 France .............................. 74.10458

[52] U.S. Cl. ................................................ 195/1.8
[51] Int. Cl.² ....................... C12B 3/00; C12K 9/00
[58] Field of Search ............................. 195/1.8, 1.7

[56] References Cited

OTHER PUBLICATIONS

Willmer—Cells and Tissues in Culture vol. 3 (1966) pp. 343–345.

*Primary Examiner*—Sam Rosen
*Attorney, Agent, or Firm*—Browdy and Neimark

[57] ABSTRACT

Process for obtaining cultures of tumoral cells in vitro, of specifically human origin.

The cultures of tumoral cells in vitro are prepared, particularly from human tumoral cells obtained from surgical samples of malignant tumors, by introducing, into the culture system, an anti-human lymphocyte serum described in the U. S. patent application Ser. No. 440,726, filed Feb. 8, 1974, which neutralizes the cytocidic and macrophagic activities of the lymphoblastoid and of the activated monocyte cells, present in the cellular system, with respect to the tumoral cells, thus permitting the establishment of continuous lines of tumoral cells in vitro.

Utilization of the continuous lines of tumoral cells in vitro thus obtained as means of elucidating the cancer process in man and as means of ascertaining the activity of new cancerostatic and cancerolytic medicaments.

9 Claims, No Drawings

PROCESS FOR OBTAINING CONTINUOUS LINES OF TUMORAL CELLS IN VITRO

The present invention relates to a process for obtaining continuous lines of tumoral cells in vitro.

The U.S. patent application Ser. No. 440,726 filed by Applicant on Feb. 8, 1974 has for its object a new immunosuppressive, anti-human lymphocyte serum, devoid of anti-erythrocyte and anti-thrombocyte action, obtained by administration to an appropriate animal of an antigenic mass essentially consisting of the acellular supernatant of one or several cultures of permanent or long-term lines initiated from human lymphocytes, or certain fractions of this supernatant. In accordance with the abovementioned patent application, the lymphocytes established in permanent lines are cultured without receiving any information other than that which is naturally specific thereto.

It is known, on the other hand, that at the time of the setting up into a culture of a surgical sample of a tumor, the culture system comprises different types of cells, such as lymphoid cells, particularly lymphocytes and monocytes, stroma cells, in particular of a fibroblastic nature, and tumoral cells.

The primocultures of tumor cells in vitro described in the prior art show rapidly confluent layers; but after this rapid multiplication phase, it is noticed that, from the fourth day onward, the tumor cells are destroyed. This effect is complete within 2 to 3 weeks and the destruction process is accentuated if it is attempted to subculture these cells with trypsin.

It has further been found that this destruction of the tumor cells occurs in every case where there is observed a very marked inherent cytotoxicity of the lymphocytes which is shown, prior to surgical intervention, on target-cells sampled from cerebral tumors in human beings (c.f. H. FEBVRE, A. MOUTTE and J. P. CONSTANS — Compte-rendus Acad. Sciences Paris 275, 2191 – 2194, No. 19, 1972: "Demonstration by using allogenic antigens, of a cell-mediated anti-tumoral immunity in man"). The cultures are rapidly overrun, from the fourth day after explantation, by large cells, having undulating membranes, which show morphological characteristics, either of lymphocytes which have developed into lymphoblastoid cells, or of active monocytes having a cytotoxic and macrophagic power. In these cases, in fact, on the one hand, the lymphoid cells transform themselves, in the presence of the tumoral antigen of the tumor cells, into lymphoblastoid cells which exert cytocidic and macrophagic actions and on the other hand, the monocytes activated by said tumoral antigen, acquire an elective cytocidic and macrophagic activity, in vitro, with respect to the tumoral cells. These two types of aggressive cells leave intact the non-tumoral cells of the support stroma. (On the subject of the definition and of the evolution of the lymphocytes and monocytes, the disclosure of Marcel BESSIS entitled "Living Blood Cells and their Ultrastructure", Springer Verlag Berlin — Heidelberg — New York, Ed., particularly pages 419 to 452 and 489 to 499, may be consulted.).

The preceding description makes it clear at which point it is difficult to obtain continuous lines established in vitro from cultures of tumoral cells originating from surgical samples of malignant tumors.

Attempts have been made with the aim of preventing the development of the reaction which destroys tumoral cells in vitro. The processes proposed in accordance with the prior art for the establishment of continuous lines of tumoral cells in vitro are of two types, namely cellular dissociation and the culture of organs. In the first type of process, one starts with a small number of tumoral cells from which is formed a selected cell line. However, this type of process is extremely slow since, even if it produces a cell proliferation every 18 hours, it must nevertheless take a long time to obtain a culture of tumoral cells established in a permanent line. With regard to the process for obtaining tumoral cells in vitro by the culture of organs, it does not allow obtaining continuous cell lines.

Nevertheless, the necessity to be able to provide pure continuous lines of tumoral cells in vitro, obtained easily, quickly and in sufficient quantities is more and more imperative. In fact, the putting of cultures of human tumoral cells in vitro, established in continuous lines, at the disposition of research workers would enable them to use the cultures to advance the elucidation of the process of cancer in man, and to evaluate the activity of new cancerostatic and cancerolytic medicaments.

The present invention has, as its aim, to provide a simple, rapid and reliable method of producing continuous lines of tumoral cells in vitro; it being impossible to achieve this object by using the techniques described in the prior art.

The present invention has for its object a process for obtaining continuous lines of tumoral cells in vitro, particularly from human tumoral cells originating in surgical samples of malignant tumors, which process is characterised in that the cultures of tumoral cells in vitro are effected in the presence of an anti-human lymphocyte serum according to abovementioned patent application, which, by neutralising the cells which are aggressive with regard to the tumoral cells, permits the establishment of continuous lines of tumoral cells in vitro.

By conforming with the process of the present invention, it is thus possible to obtain continuous lines of human tumoral cells in vitro, the process showing excellent characteristics of reliability, reproducibility, and constancy in its results.

The process which forms the object of the present invention permits the very fast establishment of tumoral cells in continuous lines, because the presence of an anti-human lymphocyte serum in accordance with the abovementioned patent application, in the culture system permits the growth of the tumoral cells to develop immediately.

The invention will be better understood with the aid of the following description which refers to Examples of carrying out of the process of the present invention. It will, nevertheless, be understood that these Examples are given solely by way of illustration and constitute no limitation of the present invention.

EXAMPLES

EXAMPLE 1

Treatment of Carcinoma Cultures by Anti-human Lymphocyte Sera

The cells of a flask of carcinoma culture are removed by trypsin and re-suspended in a Moore medium RPMI 1640 with 2% of decomplemented calf serum.

These cells are apportioned into test tubes in aliquot portions corresponding to $5.10^4$ cells in 0.5 ml of medium. There is then added 1 ml of an anti-lymphocyte serum, diluted to 1/100 in the culture medium in the course of half an hour, followed by 0.5 ml of lyophilised rabbit complement diluted to 1/20 in the culture medium in the course of 90 minutes. The tubes are maintained at 37° C on a bain-marie and the pH is adjusted to between 7.2 and 7.4. Each sample is paired with a complementless control.

The test tubes are then centrifuged. The cells are resuspended in 2 ml of culture medium additionally containing 15% of fetal calf serum. Each sample is cultured on Macrotest (Greiner) plates.

The cultures are allowed to incubate for from 24 to 48 hours in a humid atmosphere containing 5% $CO_2$. The cultures are then observed with an inversion, phase-contrast microscope having a Wild 6X phase objective.

Four sera have been tested, the readings being performed as blind readings.

1. AU 55, anti-horse serum, hyperimmunised with normal human thymus lymphocytes,
2. AU 56, anti-horse serum, hyperimmunised with peripheral blood lymphocytes cultured in continuous lines (a mixture of five different lines),
3. AU 59, anti-horse serum, hyperimmunised with the supernatant of these five (AU 56) cultures of lymphocytes, prepared in accordance with the process described in the abovementioned patent application,
4. AU 61, anti-horse serum prepared in the same manner as AU 59. Among the cultures treated by the anti-lymphocyte serum, in the presence of complement, one notices the disappearance of the cytocidic cells in the cultures treated with sera AU 59 and AU 61. This action is far less apparent with the two other sera tested (AU 55 and AU 56) and does not appear to be very specific. In fact, there is noticed a certain cytotoxicity at the level of the tumoral cells.

In the control samples without complement, there is no cytotoxicity. The cultures without anti-lymphocyte serum made in the presence of complement verify that the complement employed is not cytotoxic at the dilution employed.

EXAMPLE 2

Obtaining of Continuous Lines

The anti-human lymphocyte serum in accordance with the abovementioned patent application proves active on the cultures of samples originating from three cases of cerebral metastases of carcinomas, exhibiting positive lymphoid reaction with the tumoral target-cells:

Cerebral metastasis of an adrenal carcinoma (T 249) cytotoxicity up to 70%

Cerebral metastasis of a breast carcinoma (T 268) cytotoxicity up to 23%

Cerebral metastitis of a thyroid carcinoma (T 272) cytotoxicity up to 16%

The carcinoma cultures have been treated directly in the culture flasks, in order to eliminate the cytocidic cells during the 1st or 2nd subcultures, thus allowing the isolation of three cell lines of carcinomas of the thyroid, of the adrenal and of the breast.

The action of the anti-serum AU 59 is very fast. On already established cultures, on slides, the typical cytotoxicity reaction on the cytocidic cells is observed, 15 to 20 minutes after the cultures treated with this serum have been contacted with the complement. There is an abrupt retraction of the nucleus which seems to separate itself from the cytoplasm.

The results obtained have been listed in the following tables:

TABLES OF RESULTS

| Names | Diagnostic | 1) Cerebral Tumors: Cytotoxicity of the Lymphocytes | Lymphoid reaction in culture | Tumoral cell lines |
|---|---|---|---|---|
| 260 Bar. | Glioblastome | 47 % | + | no |
| 261 Col. | Glioblastome | 28 % | + | no |
| 267 Cho. | Astrocytome malignant | 42% | + | no |
| 271 Bre. | Glioblastome | 0 | − | yes |
| 274 Lah. | Glioblastome | 57% | + | no |
| 267 Duf. | Astrocytome malignatic | 0 | − | yes |
| | 2) Non-Cerebral Tumors and Metastases: | | | |
| 249 Ala. | Carcinoma, metast. (adrenal) | 71% | +++ | yes (serum AU 59) |
| 263 Sam. | Carcinoma, metast. (breast) | 67 % | ++ | no |
| 265 Roz. | (Carcinoma, metast. (breast) | 26% | + | no |
| 268 Eng. | Carcinoma, metast. (breast) | 23 % | + | yes (serum AU 59) |
| 270 Lao. | Sarcoma | 22 % | + | no |
| 272 Oud. | Carcinoma, metast. (thyroid) | 16 % | + | yes (serum AU 59) |
| 273 Vor. | Rabdomyosarcome | 0 | − | yes |

In conclusion it will be seen from the above tables that only either the tumoral cells of surgical samples originating from patients not showing the proper cytotoxicity of their lymphoid cells with respect to the target-cells possessing a tumoral antigen, or the tumoral cells cultured in the presence of an anti-human lymphocyte serum prepared in accordance with the process described in the abovementioned patent application, can be established in continuous lines.

It will be seen from the preceding description that, by putting the teachings of the present invention into effect, a process for the preparation of continuous lines of tumoral cells in vitro is attained, even though this had been impossible hitherto. The preparation in accordance with the present invention ensures the conditions of speed, purity, reliability and constancy which are necessary.

What I claim is:

1. Process for obtaining continuous lines of human tumoral cells in vitro, originating from surgical samples of malignant tumors in which there is an inherent cytotoxicity of the lymphocytes, comprising:

culturing said human malignant tumoral cells in vitro in the presence of an immunosuppressive anti-human lymphocyte serum devoid of anti-erythrocyte and anti-thrombocyte action, obtained from the supernatant of cultures of lymphocytes established in long-term lines initiated from human lymphocytes, said serum neutralizing the cytocidic and macrophagic activities of the lymphoblastoid and of the active monocyte cells present in the cellular system, with respect to said human malignant cells, thus permitting the establishment of continuous lines of said human malignant tumoral cells in vitro.

2. Process according to claim 1, characterised in that the cultures of human malignant tumoral cells in vitro are treated with the anti-human lymphocyte serum in the presence of complement.

3. Process according to claim 1 characterised in that the cultures of tumoral cells in vitro are treated with said anti-human lymphocyte serum in the presence of stimulating agents which increase the concentration of the tumoral cells in the cultures.

4. Pure continuous lines of human malignant tumoral cells contained in an in vitro culture media obtained by utilising the process as claimed in claim 1.

5. Pure continuous lines of human malignant tumoral cells contained in an in vitro culture media obtained according to the process of claim 2.

6. Pure continuous lines of human malignant tumoral cells contained in an in vitro culture media obtained according to the process of claim 3.

7. A process in accordance with claim 1 wherein said human malignant tumoral cells are carcinoma cells.

8. A process in accordance with claim 7 wherein said carcinoma cells are cerebral metastases from adrenal carcinoma, breast carcinoma or thyroid carcinoma.

9. A process in accordance with claim 1 wherein said human malignant tumoral cells are glioblastome cells, astrocytome malignant cells or sarcoma cells.

* * * * *